United States Patent
Zhang et al.

(10) Patent No.: US 10,391,480 B2
(45) Date of Patent: Aug. 27, 2019

(54) METHODS OF PRODUCING HIERARCHICAL BETA ZEOLITES WITH TUNABLE MESOPOROSITY THROUGH PORE DIRECTING AGENT ASSISTED BASE LEACHING

(71) Applicant: Saudi Arabian Oil Company, Dhahran (SA)

(72) Inventors: Ke Zhang, Stoneham, MA (US); Sergio Fernandez, Somerville, MA (US)

(73) Assignee: Saudi Arabian Oil Company, Dhahran (SA)

( * ) Notice: Subject to any disclaimer, the term of this patent is extended or adjusted under 35 U.S.C. 154(b) by 129 days.

(21) Appl. No.: 15/583,380

(22) Filed: May 1, 2017

(65) Prior Publication Data

US 2018/0311652 A1 Nov. 1, 2018

(51) Int. Cl.

| | | |
|---|---|---|
| *B01J 29/06* | (2006.01) | |
| *B01J 29/70* | (2006.01) | |
| *B01J 35/10* | (2006.01) | |
| *B01J 37/00* | (2006.01) | |
| *B01J 37/04* | (2006.01) | |
| *C01B 39/48* | (2006.01) | |
| *C01B 39/02* | (2006.01) | |
| *C07C 5/25* | (2006.01) | |
| *B01J 29/04* | (2006.01) | |
| *B01J 37/10* | (2006.01) | |

(52) U.S. Cl.
CPC ......... *B01J 29/7007* (2013.01); *B01J 29/041* (2013.01); *B01J 35/109* (2013.01); *B01J 35/1023* (2013.01); *B01J 35/1057* (2013.01); *B01J 35/1061* (2013.01); *B01J 37/0018* (2013.01); *B01J 37/04* (2013.01); *B01J 37/10* (2013.01); *C01B 39/026* (2013.01); *C01B 39/48* (2013.01); *C07C 5/2518* (2013.01); *B01J 2229/10* (2013.01); *B01J 2229/30* (2013.01); *B01J 2229/34* (2013.01); *B01J 2229/36* (2013.01); *B01J 2229/38* (2013.01); *C01P 2006/12* (2013.01); *C01P 2006/16* (2013.01); *C07C 2529/70* (2013.01)

(58) Field of Classification Search
CPC .. B01J 29/041; B01J 29/7007; B01J 2229/10; B01J 2229/30; B01J 2229/34; B01J 2229/36; B01J 2229/38; B01J 35/1023; B01J 35/1061; B01J 35/1057; B01J 35/109; B01J 37/0018; B01J 37/04; B01J 37/10; C01B 39/48; C01B 39/026
USPC ........ 502/60, 76, 85, 86; 423/701, 702, 704, 423/705, 716
See application file for complete search history.

(56) References Cited

U.S. PATENT DOCUMENTS

| | | | |
|---|---|---|---|
| 7,589,041 B2 * | 9/2009 | Ying ........................ | B01J 20/18 502/63 |
| 8,486,369 B2 | 7/2013 | Garcia-Martinez et al. | |
| 8,524,624 B2 * | 9/2013 | Garcia-Martinez ...... | B01J 20/18 423/700 |
| 8,685,875 B2 * | 4/2014 | Garcia-Martinez ...... | B01J 29/04 423/700 |
| 2005/0239634 A1 * | 10/2005 | Ying ........................ | B01J 20/18 502/64 |
| 2012/0258852 A1 | 10/2012 | Martinez et al. | |

FOREIGN PATENT DOCUMENTS

WO 2016196267 A1 12/2016

OTHER PUBLICATIONS

International Search Report and Written Opinion dated Jun. 8, 2018, for International Application No. PCT/US2018/027731, filed Apr. 16, 2018, 17 pages.
Li et al., "Realizing the Commercial Potential of Hierarchical Zeolites: New Opportunities in Catalytic Cracking", ChemCatChem, 2014, 6, 46-66, Wiley-VCH Verlag GmbH & Co.
Mitchell et al., "Structural Analysis of Hierarchically Organized Zeolites", Nature Communications, 2015, 6: 8633, Macmillan Publishers Limited.
Roth et al., "A Family of Zeolites with Controlled Pore Size Prepared Using a Top-Down Method", Nature Chemistry, 2013, 5, 628-633, Macmillan Publishers Limited.
Verboekend et al., "Mesopore Formation in USY and Beta Zeolites by Base Leaching: Selection Criteria and Optimization of Pore-Directing Agents", Crystal Growth & Design, 2012, 12, 3123-3132, American Chemical Society.
Verboekend et al., "Hierarchical Y and USY Zeolites Designed by Post-Synthetic Strategies", Adv. Fund. Mater., 2012, 22, 916-928, Wiley-VCH Verlag GmbH & Co.
Zhang et al., "Optimization of Hierarchical Structures for Beta Zeolites by Post-Synthetic Base Leaching", Ind. Eng. Chem. Res., 2016, 55, 8567-8575, American Chemical Society.

* cited by examiner

*Primary Examiner* — Elizabeth D Wood
(74) *Attorney, Agent, or Firm* — Dinsmore & Shohl LLP

(57) ABSTRACT

Methods for producing mesoporous beta zeolites from parent beta zeolites having a Si/Al molar ratio of at least 10 comprise selecting a target average mesoporous size between 2 nm and 8 nm for the parent beta zeolites, selecting a pore directing agent (PDA) based on the target average mesopore size, where a non-ionic surfactant, a small cationic surfactant has a molecular weight of greater than 100 grams/mole, or both may be selected as the PDA when the target average mesopore size is at least 5 nm, and a large cationic surfactant having a molecular weight of less than 100 grams/mole may be selected as the PDA when the target average mesopore size is less than 5 nm. The method further comprises adding the selected PDA to an alkaline solution to form a PDA-base mixture, and adding the parent beta zeolites to the PDA-base mixture to produce the mesoporous beta zeolites.

31 Claims, 10 Drawing Sheets

METHODS OF PRODUCING HIERARCHICAL BETA ZEOLITES WITH TUNABLE MESOPOROSITY THROUGH PORE DIRECTING AGENT ASSISTED BASE LEACHING

TECHNICAL FIELD

The present disclosure generally relates to methods of producing mesoporous beta zeolites, and specifically relates to methods of imparting and controlling mesoporosity in mesoporous beta zeolites (also referred to as hierarchical beta zeolites) through pore directing agent (PDA) assisted base leaching.

BACKGROUND

Zeolites are crystalline aluminosilicates constructed by $AlO_4$ or $SiO_4$ tetrahedra with various framework structures that are extensively applied in adsorption, catalysis and separation. Generally, conventional zeolites are composed of 8, 10, or 12-membered-ring (12-MR) pore channels with pore sizes less than 1 nm. Due to their excellent stability, strong acidity and regular pore sizes, these microporous crystalline materials are of great importance to industrial catalysis as heterogeneous catalysts in petrochemical and chemical conversion processes. However, when large species with sizes similar with or greater than the dimensions of the pores in zeolites are involved in a catalytic conversion, the active sites in zeolites tend to become inaccessible due to strong diffusion limitation or molecular rejection induced by the relatively rigid zeolite micropore structure, which results in a less effective use of zeolite catalysts. Moreover, the diffusion limitation of reaction products or intermediates also increases the possibility of coking, or changes in desired product distribution.

To alleviate these challenges, the concept of hierarchical zeolites were suggested to introduce at least one additional pore system, usually in the mesopore range (i.e. mesoporous zeolites), in conventional zeolites. Zeolite beta has a three-dimensional network of 12-MR pores featuring an intergrowth of two or more polymorphs with pore diameters of 0.55×0.55 nm and 0.76×0.64 nm and is one of the several most important zeolites in the refining and fine chemical industries. Various strategies have been reported for the synthesis of hierarchical beta zeolites. Hierarchical beta structures with tunable mesoporosity have been synthesized with various mesopore templates, such as cationic polymers (i.e., polydiallyldimethylammonium chloride) and ammonium modified chitosan or structured organosilanes with different functional groups.

The presence of mesopore templates usually enhance the interaction within silicate species and avoid phase separation during the process of "mesopore template-zeolite structure directing agent" dual-templating synthesis. Alternatively, hierarchical beta structure with intercrystalline mesopores is assembled without using mesopore templates by nanocrystal aggregation in a dry-gel conversion process.

Hierarchical MFI and Y zeolite structures have been obtained by direct base leaching of microporous MFI and Y zeolites. This method is usually referred as a top-down approach or desilication. In the top-down approach, mesoporosity is created by partial dissolution and recrystallization of the zeolite framework in an alkaline solution. However, the framework of zeolite beta is less stable than MFI zeolites, and amorphization easily occurs for high Si beta zeolites during NaOH leaching, which may negatively impacts the microporosity and acidity of the resulting products. Moreover, it is not clear how to manipulate the mesopore sizes of mesoporous beta zeolites by the top-down approach.

BRIEF SUMMARY

Accordingly, there is a need for improved methods for making mesoporous beta zeolites with controllable average mesopore sizes without damaging the zeolite beta framework by using the top-down approach.

Embodiments of the present disclosure meet this need by utilizing a pore directing agent (PDA) assisted based leaching process—also referred to as a top-down approach or desilication—in order to impart mesoporosity to the zeolite beta framework. The resulting mesoporosity is created by the partial dissolution and recrystallization of the zeolite framework in the alkaline solutions. Specifically, it was found that cationic and non-ionic surfactants are effective PDAs in directing the mesopore formation in alkaline solutions without experiencing significant decrease in microporosity and crystallinity of parent beta zeolites. PDAs provide protection of zeolite beta frameworks by preferential interaction with zeolites while simultaneously directing the mesopore formation in the alkaline solution.

As compared to the mesopore templating/template free routes, the top-down approach has the advantages of being highly reproducible, convenient, and cost effective. Moreover, it was discovered that mesopore size in beta zeolites can be tailored by top-down base leaching through the appropriate selection of PDA. This tailorability is produced by the discovered structure property relationship between PDA surfactant type, PDA structure, and average mesopore size in resulting hierarchical zeolites.

By applying different cationic or non-ionic surfactants with various molecular weights and/or structures, the average mesopore sizes can be manipulated and reproducibly controlled in the size range of 2-8 nm. Generally, larger cationic surfactants lead to zeolite materials with smaller average mesopore sizes and smaller cationic surfactants lead to zeolite materials with larger average mesopore sizes, while mesoporous beta zeolites via base leaching with non-ionic surfactants possess larger mesopores than those treated with cationic surfactants. Application of the methods described herein allow for the generation of hierarchical beta zeolite materials with controlled average mesopore sizes (e.g., from 2-8 nm) and BET surface areas (500-800 $m^2/g$) through the use of the appropriate pore directing agent.

In some embodiments, provided herein is a method for producing mesoporous beta zeolites comprising: providing parent beta zeolites having a molar ratio of silicon to aluminum of at least 10; selecting a target average mesopore size between 2 nm and 8 nm for the parent beta zeolites; selecting a pore directing agent (PDA) based on the target average mesopore size, where a non-ionic surfactant, a small cationic surfactant, or both may be selected as the PDA when the target average mesopore size is at least 5 nm, and a large cationic surfactant may be selected as the PDA when the target average mesopore size is less than 5 nm, where the large cationic surfactant has a molecular weight of greater than 100 grams/mole, and the small cationic surfactant has a molecular weight of less than 100 grams/mole; adding the selected PDA to an alkaline solution to form a PDA-base mixture; and adding the parent beta zeolites to the PDA-base mixture to produce the mesoporous beta zeolites having an average mesopore size corresponding to the target average mesopore size.

In other embodiments, provided herein is a method for producing mesoporous beta zeolites comprising: providing parent beta zeolites having a molar ratio of silicon to aluminum of at least 10; adding a pore directing agent (PDA) comprising cationic surfactant having a molecular weight of more than 100 grams/mole to an alkaline solution to form a PDA-base mixture; and adding the parent beta zeolites to the PDA-base mixture to produce the mesoporous beta zeolites having an average mesopore size of less than 5 nm.

In yet other embodiments, provided herein is a method for producing mesoporous beta zeolites comprising: providing parent beta zeolites having a molar ratio of silicon to aluminum of at least 10; adding pore directing agent (PDA) comprising cationic surfactant having a molecular weight of less than 100 grams/mole to an alkaline solution to form a PDA-base mixture; and adding the parent beta zeolites to the PDA-base mixture to produce the mesoporous beta zeolites having an average mesopore size of at least 5 nm.

In still other embodiments, provided herein is a method of for producing mesoporous beta zeolites comprising: providing parent beta zeolites having a molar ratio of silicon to aluminum of at least 10; adding a non-ionic amine pore directing agent (PDA) having at least 2 carbon atoms to an alkaline solution to form a PDA-base mixture; and adding the parent beta zeolites to the PDA-base mixture to produce the mesoporous beta zeolites having an average mesopore size greater than 2 nm.

In various specific embodiments, the molar ratio of silicon to aluminum is from 14 to 250, or from 14 to 300, or from 50 to 250.

In some embodiments, the selected PDA is the non-ionic surfactant, the non-ionic surfactant being an amine compound having more than 2 carbon atoms. In specific embodiments, the amine compound has from 2 to 6 carbon atoms.

In some embodiments, the PDA is a large cationic surfactant comprising dodecyltrimethylammonium, cetyltrimethylammonium, propyltrimethylammonium, tetraethylammonium, tetrapropylammonium, octyltrimethylammonium, or combinations thereof.

In some embodiments, the PDA is a non-ionic surfactant comprising monoamines, polyamines, or combinations thereof. In specific embodiments, the non-ionic surfactant comprising ethylenediamine, diaminohexane, trisaminoethylamine, diethylamine, or combinations thereof.

In some embodiments, the large cationic surfactant and the small cationic surfactant are quaternary ammonium compounds. In specific embodiments, the PDA comprises tetramethylammonium.

In various embodiments, the alkaline solution comprises NaOH, KOH, or CsOH. In specific embodiments, the alkaline solution comprises NaOH.

In some embodiments, the mesoporous beta zeolites have a BET surface area greater than 700 $m^2/g$ and the average mesopore size is less than 5 nm. In other embodiments, the mesoporous beta zeolites have a BET surface area less than 700 $m^2/g$ and the average mesopore size is at least 5 nm.

BRIEF DESCRIPTION OF THE DRAWINGS

The following detailed description of specific embodiments of the present disclosure can be best understood when read in conjunction with the following drawings, where like structure is indicated with like reference numerals and in which.

Reference will now be made in greater detail to various embodiments, some embodiments of which are illustrated in the accompanying drawings. Whenever possible, the same reference numerals will be used throughout the drawings to refer to the same or similar parts.

DETAILED DESCRIPTION

Figure 1:
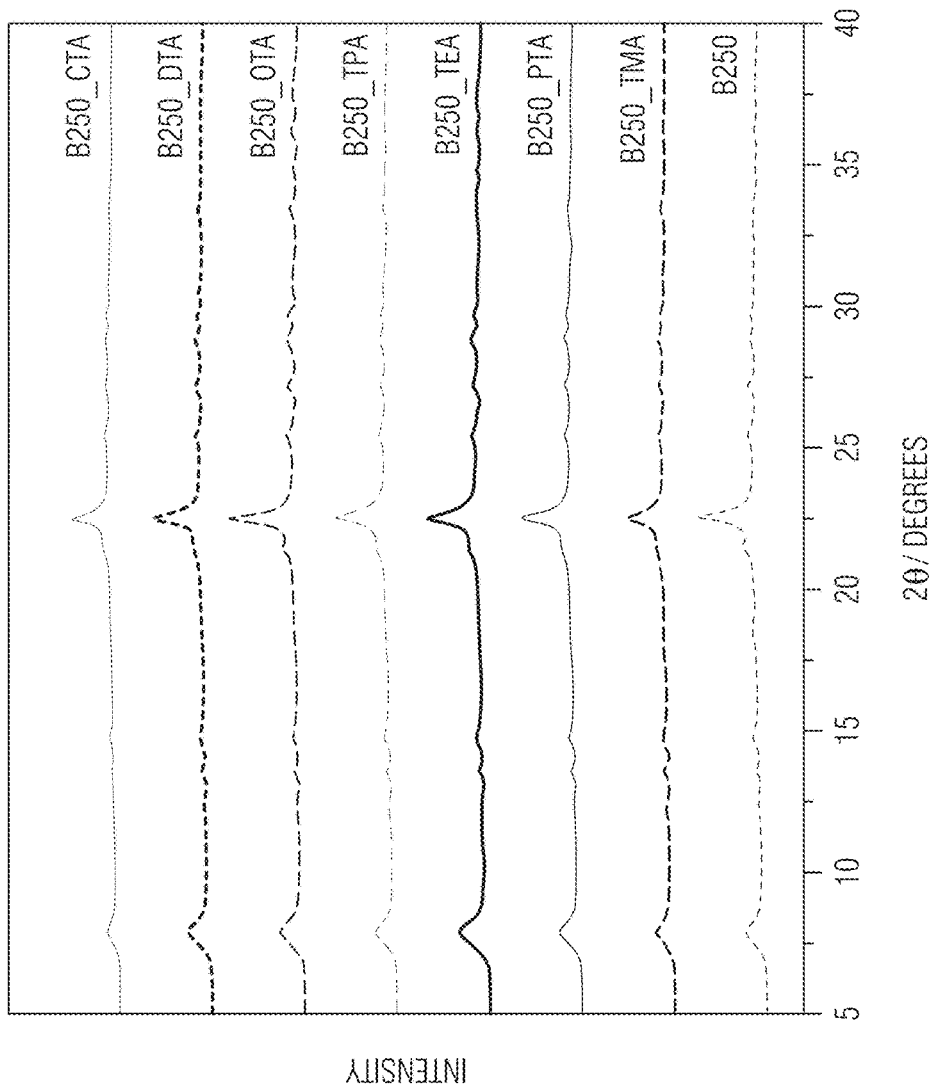
FIG. 1 depicts Powder X-Ray Diffraction (XRD) patterns of B250 series beta zeolites with cationic surfactants, according to some embodiments of the disclosure. The "B" means beta and the number is the Si/Al ratio, thus B250 means a Si/Al ratio of 250.

Embodiments of the present disclosure are directed to embodiments for producing mesoporous beta zeolites using the top-down approach, i.e. pore directing (PDA) assisted base leaching. Under the top-down approach, mesopores are created via partially dissolving the zeolite framework by desilication. The methods comprise a starting material of parent beta zeolites having a molar ratio of silicon to aluminum of at least 10, 10-∞ (where ∞ refers to silicon beta), 10-250, or 14-300. As stated above, a target average mesopore size between 2 nm and 8 nm for the mesoporous beta zeolites generated by these methods is possible. This top-down approach is believed to be destructive and less controllable, as compared to those templating approaches (bottom-up approach). Despite these concerns regarding amorphization with beta zeolites as well as concerns regarding mesoporosity control, it was surprisingly found that PDA assisted base leaching using a rational PDA selection process achieves mesoporous beta zeolites with controllable mesopore sizes without excessive destruction of the parent beta zeolite framework.

In accordance with the present embodiments, the rational selection entails selecting a pore directing agent (PDA) based on the target average mesopore size. In accordance with this rational selection, a non-ionic surfactant, a small cationic surfactant, or both may be selected as the PDA when the target average mesopore size is at least 5 nm, and a large cationic surfactant may be selected as the PDA when the target average mesopore size is less than 5 nm. Here, the large cationic surfactant has a molecular weight of greater than 100 grams/mole, and the small cationic surfactant has a molecular weight of less than 100 grams/mole.

Without being bound by theory, the average mesopore size in beta zeolites can be tailored by top-down base leaching using the appropriate selection of the PDAs described above. PDAs are typically applied to protect a zeolite framework that is sensitive to excessive base leaching when undergoing direct mesopore formation in alkaline solutions. All previous work found in the literature only focuses on the effectiveness of the PDA and whether the applied PDA can protect the parent zeolite framework. As described herein, it is now possible to manipulate and control the average mesopores sizes by selecting different PDAs during the PDA assisted base leaching.

The method embodiments also include the steps of adding the selected PDA to an alkaline solution to form a PDA-base mixture, and adding the parent beta zeolites to the PDA-base mixture to produce the mesoporous beta zeolites having an average mesopore size corresponding to the target average mesopore size.

As used herein, "parent beta zeolites" refers to the microporous beta zeolites structure prior to undergoing the PDA assisted base leaching which imparts the mesopores to the beta zeolites. The parent beta zeolites (also called zeolite beta) are aluminosilicate zeolites having a silicon to aluminum molar ratio of at least 10, or from 10-co, or greater than 500, or from 100 to 1000, or from 10 to 10000, or from 14 to 300, or from 50 to 250. As used herein, a "high Si" beta zeolite has a silicon-to-aluminum molar ratio greater than 10. While parent beta zeolites with these higher Si/Al molar ratios are less stable and sensitive to NaOH leaching, the addition of the PDA surfactant solutions direct the formation of mesopores while preventing amorphization of zeolite framework. The beta zeolites may have a crystal size from about 0.1 to 0.7 μm, and a BET surface area of at least 500 $m^2/g$, or from 500 to 800 $m^2/g$, or from 600 to 1000 $m^2/g$, or from 700 to 800 $m^2/g$.

As used throughout this disclosure, "zeolites" refer to micropore-containing inorganic materials with regular intracrystalline cavities and channels of molecular dimension. The microporous structure of zeolites (for example, 0.3 nm to less than 2 nm pore size) may render large surface areas and desirable size-/shape-selectivity, which may be advantageous for catalysis. In embodiments, the zeolites described may include micropores (present in the microstructure of a zeolite), and additionally include mesopores. As used throughout this disclosure, micropores refer to pores in a structure that have a diameter of less than or equal to 2 nm and greater than or equal to 0.1 nm, and mesopores refer to pores in a structure that have a diameter of greater than 2 nm and less than or equal to 50 nm.

As described throughout, the present embodiments utilize an alkaline solution for the PDA assisted base leaching process. Various bases are contemplated for use in the alkaline solution. In one or more embodiment, the base may comprise an alkali metal base, for example, NaOH.

Various cationic surfactants, whether large cationic surfactants or small cationic surfactants, are contemplated as suitable for use as PDAs. As used herein, "large cationic surfactant" refers to a cationic surfactant having a molecular weight of greater than 100 grams/mole, whereas "small cationic surfactant" refers to a cationic surfactant having a molecular weight of less than 100 grams/mole. In one or more embodiments, the large cationic surfactant and the small cationic surfactant may each include quaternary ammonium compounds.

For example and not way of limitation, the large cationic surfactants may comprise dodecyltrimethylammonium ($DTA^+$), cetyltrimethylammonium ($CTA^+$), propyltrimethylammonium ($PTA^+$), tetraethylammonium ($TEA^+$), tetrapropylammonium (TPA), octyltrimethylammonium ($OTA^+$), or combinations thereof. The structures for $DTA^+$ and $CTA^+$, which are depicted in Table 2 below, include long hydrocarbon chains of at least 10 carbons bonded to the amine. In further embodiments, small cationic surfactant may comprise tetramethylammonium ($TMA^+$), or a combination of $TMA^+$ with one or more large cationic surfactants.

Similarly, various non-ionic surfactants are also considered suitable for use as PDAs. In one or more embodiments, the non-ionic surfactants may comprise an amine compound having at least 2 carbon atoms, or from 2 to 6 carbon atoms. Moreover, the non-ionic surfactants may comprise monoamines, polyamines, or combinations thereof. These polyamines may include secondary amines or tertiary amines. For example and not by way of limitation, the non-ionic surfactants may comprise ethylenediamine (EDA), diaminohexane (DAH), trisaminoethylamine (TAEA), diethylamine (DEA), or combinations thereof.

The mesopores of the presently disclosed mesoporous beta zeolites may have an average size of from 2 nm to 8 nm. In some embodiments, the majority of the mesopores may be greater than 2 nm, or greater than 4 nm. The large cationic surfactants may yield mesoporous beta zeolites with average mesopore sizes below 5 nm, or from 2 to 4 nm. In addition to producing these smaller mesopores, the large cationic surfactants may yield a larger BET surface area for mesoporous beta zeolites, for example, a BET surface area greater than 700 $m^2/g$, or greater than 750 $m^2/g$.

In various embodiments, the small cationic surfactants may yield mesoporous beta zeolites with larger average mesopore sizes, for example, at least 4 nm, or at least 5 nm, or from 4 to 6 nm. While producing these larger mesopores, the small cationic surfactants yield a smaller BET surface area for mesoporous beta zeolites, for example, a BET surface area less than 700 $m^2/g$, or less than 650 $m^2/g$. Stated another way, the created average mesopore sizes and surface areas are correlated with the molecular weights of the different cations, i.e. higher molecular weight cations result in smaller average mesopore size and correspondingly larger surface areas.

Mesoporous beta zeolites (hierarchical structures) produced from non-ionic surfactants possess an average mesopore size of at least 2 nm, or at least 5 nm, or from 5 to 8 nm. In many instances, the average mesopore size will be larger for mesoporous beta zeolites produced from non-ionic surfactants as compared to the average mesopore size produced from cationic surfactants. Without being bound by theory, this is likely due to better accommodation of cationic surfactants within the inner channels of the beta zeolite framework and more favorable interaction and protection of parent framework as compared to non-ionic amine surfactants.

Without being bound by theory, it is believed that micelle formation occurs for some of the large cationic surfactants. This can be seen from the significant differences in the pore size distributions seen in FIG. 3 for the larger cationic surfactants ($CTA^+$, $DTA^+$) as compared to the smaller ones. $OTA^+$, which is smaller than $DTA^+$, does not seem to undergo micelle formation and follows a similar trend as the other cationic surfactants.

It is also believed that the mesopores are being formed in between the spaces of the surfactant molecules that are attaching to the surface of the beta zeolites. With large surfactants attaching to the surface, there is less exposed space on the zeolites for OH— hydrolysis to occur—which results in smaller average mesopore sizes formed using this method.

In one or more other embodiments, the mesoporous beta zeolites may have total pore volumes of greater than or equal to 0.2 cm$^3$/g, greater than or equal to 0.25 cm$^3$/g, greater than or equal to 0.3 cm$^3$/g, greater than or equal to 0.35 cm$^3$/g, greater than or equal to 0.4 cm$^3$/g, greater than or equal to 0.45 cm$^3$/g, greater than or equal to 0.5 cm$^3$/g, greater than or equal to 0.55 cm$^3$/g, greater than or equal to 0.6 cm$^3$/g, greater than or equal to 0.65 cm$^3$/g, or even greater than or equal to 0.7 cm$^3$/g, and less than or equal to 1.5 cm$^3$/g.

In further embodiments, the portion of the surface area contributed by mesopores of the mesoporous beta zeolites may be greater than or equal to 20%, greater than or equal to 25%, greater than or equal to 30%, greater than or equal to 35%, greater than or equal to 40%, greater than or equal to 45%, greater than or equal to 50%, greater than or equal to 55%, greater than or equal to 60%, or even greater than or equal to 65%, such as between 20% and 70% of total surface area.

The mesoporous beta zeolites described may form as particles that may be generally spherical in shape or irregular globular shaped (that is, non-spherical). In embodiments, the particles have a "particle size" measured as the greatest distance between two points located on a single zeolite particle. For example, the particle size of a spherical particle would be its diameter.

In other shapes, the particle size is measured as the distance between the two most distant points of the same particle, where these points may lie on outer surfaces of the particle. The particles may have a particle size from 25 nm to 500 nm, from 50 nm to 400 nm, from 100 nm to 300 nm, or less than 900 nm, less than 800 nm, less than 700 nm, less than 600 nm, less than 500 nm, less than 400 nm, less than 300 nm, or less than 250 nm. In some embodiments, the particles may have a particle size of or greater than 900 nm, greater than 800 nm, greater than 700 nm, greater than 600 nm, greater than 500 nm, greater than 400 nm, greater than 300 nm, or greater than 250 nm. Particle sizes may be visual examination under a microscope.

The mesoporous beta zeolites described in the present disclosure can be applied to many industrially valuable processes. These processes include fluidization processes (such as fluidized catalytic cracking (FCC), deep catalytic cracking (DCC), and high severity fluidized catalytic cracking (HSFCC)), dehydrogenation process, isomerization process, and reforming process. Using the present mesoporous beta zeolites generated through this method as opposed to using the conventional microporous zeolites is expected to result in improved performance (e.g., higher conversion) for these reactions. Specifically, the high mesoporosity allows for greater catalytic functionality because more micropores are available for contact with the reactant in a catalytic reaction. The mesopores allow for better access to microporous catalytic sites on the mesoporous zeolite.

Additionally, having the ability to manipulate the surface area, mesopore size, and catalytic activity through the use of this disclosure can allow for optimization of the reactions. As compared to the parent beta catalysts, the successful introduction of mesopores in beta zeolites has led to a significantly improved catalytic conversion for the acid-catalyzed alpha-pinene isomerization.

EXAMPLES

The various embodiments of methods described will be further clarified by the following examples. The examples are illustrative in nature, and should not be understood to limit the subject matter of the present disclosure.

Example 1

The parent beta zeolites, provided by TOSOH Corporation, were coded as "Bx", where "x" refers to the nominal Si/Al ratios. These zeolites were in their protonic form. All base leaching treatments were carried out at 65° C. for 30 min. In a typical experiment, the alkaline solution (0.2M NaOH+0.2M PDA, 1:1 mixture) was stirred at 400 rpm and heated to 65° C. before the parent zeolite samples were added in the amounts of 3.3 g zeolites per 100 ml solution The leached samples in the suspension were retrieved by quenching, centrifuging, washing with distilled water, and drying overnight at 110° C. The leached samples are labeled as "Bx_PDA's acronym" and "NaOH" is omitted for brevity. PDA's acronym is defined in Table 2.

TABLE 2

SURFACTANT MOLECULES USED IN NAOH BASE LEACHING AS PORE DIRECTING AGENTS

| Chemical | Name | Structure | Formula | Counterion |
|---|---|---|---|---|
| Cationic Surfactants | | | | |
| TMA$^+$ | Tetramethylammonium | 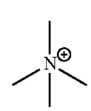 | $(CH_3)_4N^+$ | $Br^\ominus$ |
| PTA$^+$ | Propyltrimethylammonium | 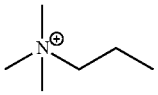 | $(CH_3)_3N^+C_3H_7$ | $Br^\ominus$ |

TABLE 2-continued

SURFACTANT MOLECULES USED IN NAOH BASE LEACHING AS PORE DIRECTING AGENTS

| Chemical | Name | Structure | Formula | Counterion |
|---|---|---|---|---|
| TEA$^+$ | Tetraethylammonium | 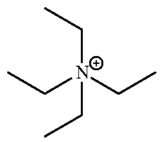 | $(C_2H_5)_4N^+$ | Br$^\ominus$ |
| TPA$^+$ | Tetrapropylammonium | 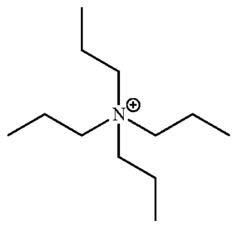 | $(C_3H_7)_4N^+$ | Br$^\ominus$ |
| OTA$^+$ | Octyltrimethylammonium | 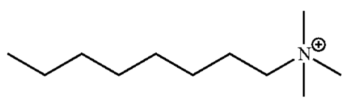 | $(CH_3)_3N^+C_{12}H_{25}$ | Br$^\ominus$ |
| DTA$^+$ | Dodecyltrimethylammonium | 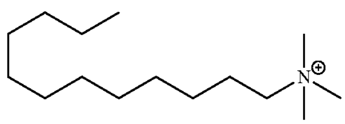 [SMILES: CCCCCCCCCCCC[N+](C)(C)C] | $(CH_3)_3N^+C_{12}H_{25}$ | Br$^\ominus$ |
| CTA$^+$ | Cetyltrimethylammonium | 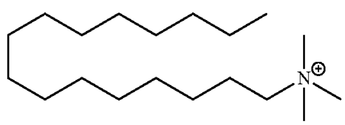 [SMILES: CCCCCCCCCCCCCCCC[N+](C)(C)C] | $(CH_3)_3N^+C_{16}H_{33}$ | Br$^\ominus$ |
| Non-Ionic Surfactants | | | | |
| EDA | Ethylenediamine | 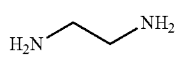 | $C_2H_4(NH_2)_2$ | — |
| DAH | Diaminohexane | 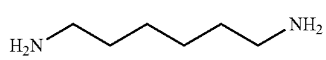 | $H_2N(CH_2)_6NH_2$ | — |
| TAEA | Trisaminoethylamine | 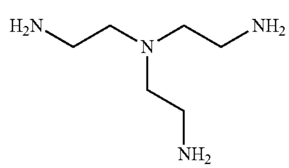 | $N(CH_2CH_2NH_2)_3$ | — |
| DEA | Diethylamine | 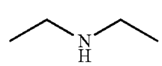 | $HN(CH_2CH_3)_2$ | — |

When an ion-exchange step was needed, the samples were transformed to the protonic form by a three-fold ammonium-exchange in 0.8 M NH$_4$NO$_3$ and a subsequent calcination at 550° C. for 5 h at a heating rate of 10° C./min.

Powder X-ray diffraction (XRD) measurements were taken using a Bruker D8 Discover diffractometer equipped with a copper tube (1=0.15418 nm) and a VANTEC-500 2-D detector. Data was recorded in the range of 5-40 2θ/degrees.

Scanning electron microscopy (SEM) imaging was done using a JEOL JSM-7100F Scanning Electron Microscope using an operating voltage of 15 kV. Nitrogen physisorption measurements were performed at −196° C. on a Micromeritics ASAP 2460. Prior to the measurements, all samples were degassed at 350° C. overnight under vacuum in a Micromeritics Smart VacPrep.

The apparent surface areas were determined with the Brunauer-Emmett-Teller (BET) method in the range between P/P$_0$ 0.02-0.12. The t-plot method was used to estimate the micropore volume (V$_{mic}$) and total pore volume (V$_{tot}$). The mesopore size distribution was obtained by the Barrett-Joyner-Halenda (BJH) model applied to the adsorption branch of the isotherm.

Fourier transform infrared (FT-IR) spectroscopy was carried out in a Nicolet iS50 FT-IR Tri-Detector Gold Flex Spectrometer with Praying Mantis diffuse reflectance accessory. The pellets were pressed by adding 1 wt % zeolite powders in KBr for a homogeneous mixture and the spectra were recorded in the range of 500-4000 cm$^{-1}$.

For the scans in the OH stretching region, the samples were preheated at 350° C. in flowing N$_2$ for 60 min. The α-pinene isomerization was carried out at atmospheric pressure in a glass reactor under magnetic stirring. In a typical run, 0.10 g catalyst and 2.0 mL of α-pinene were applied to react at 70° C. for 30 min.

After the reaction, the solid catalyst was filtered and the remaining liquid was analyzed using an Agilent 7890B gas chromatograph equipped with a Restek Rtx-1 30 m capillary column and interfaced to a JEOL AccuTOFX mass spectrometer with a field-ionization ion source.

Results and Discussion

FIG. 1 shows the XRD patterns for various B250 beta zeolites. The crystalline structures were maintained for all PDA-assisted alkaline treated samples. All of the cationic and non-ionic surfactants served as effective PDAs in protecting the parent beta framework and directing mesopore formation during the base leaching process. The characteristic peaks are distinct and well maintained (at 2θ around 7 and 22.5°) as compared to parent B250.

Beta zeolites with Si/Al >20 are very susceptible to amorphization in NaOH solutions. Accordingly, these zeolites readily lost their characteristic XRD peaks with severe framework degradation upon NaOH desilication under similar basicity as in this work. Thus, when Si/Al >20, a PDA is added to protect the beta zeolite during base leaching, while for beta with Si/Al <20, i.e. B14, mesopores can be created in NaOH alone without adding PDA. In the instance, if PDA is added, one can slightly manipulate the pore size, but the addition is not required in terms of protecting the parent zeolite.

XRD results indicate that, for high Si beta B250, the selection of PDAs is not limited to cationic surfactants. Rather, non-ionic surfactants are also effective PDA candidates in the process of PDA-assisted base leaching.

Figure 3:
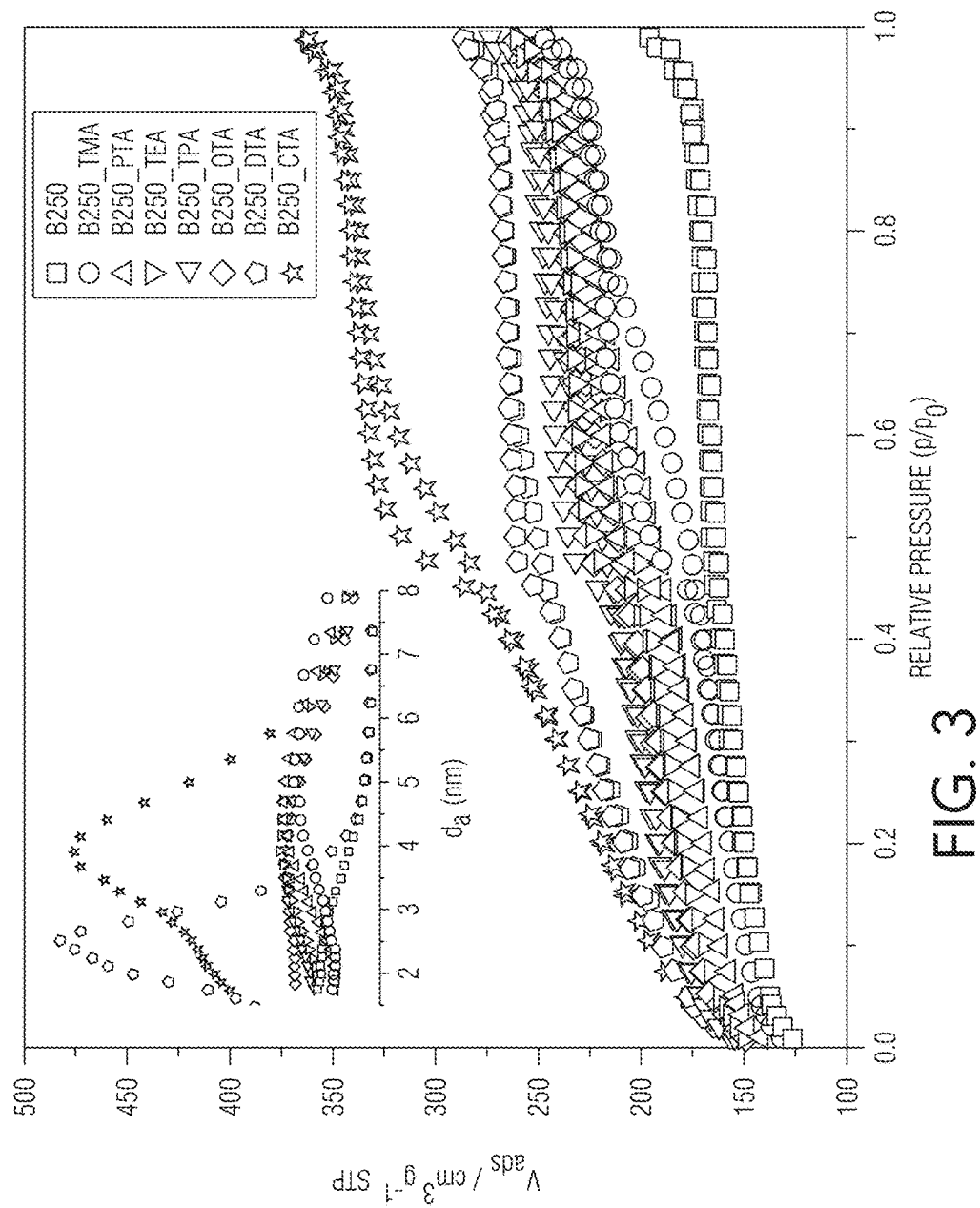
FIG. 3 depicts $N_2$ sorption isotherms of B250 series beta zeolites with cationic surfactants, according to some embodiments of the disclosure, wherein the insets illustrate the mesopore size distribution estimated by the Barrett-Joyner-Halenda (BJH) method.

The $N_2$ physisorption isotherm showed large uptakes at low relative pressures (<0.1) with limited uptake increase at higher $P/P_o$ for original microporous beta B250 (See, FIG. 3). Upon base leaching in alkaline solutions containing cationic surfactants as PDAs (e.g., tetraalkyl ammonium (TAA) cations), all isotherms exhibited slightly higher initial $N_2$ uptakes at $P/P_o$<0.1. This indicates that the microporosity is very well preserved without degradation during the alkaline treatments.

The slight increase in initial $N_2$ uptake was possibly due to zeolite recrystallization in the presence of PDAs around local areas partially dissolved in alkaline solutions initially. As revealed by XRD and $N_2$ physisorption isotherms, the preservation of microporosity results directly from the presence of TAA cations in the alkaline solutions, likely because these cations protect zeolite beta structures from excessive dissolution via preferential interaction with the zeolite framework.

The alkaline treated zeolites showed enhanced uptakes in the medium-to-high $P/P_o$ (>0.4) and the creation of mesoporosity is revealed by distinct desorption hysteresis starting around 0.4 $P/P_o$. Hierarchical zeolites exhibit H-4 desorption hysteresis loops commonly associated with hierarchical structures with micropores, mesopores and solid materials with the presence of narrow slit-like pores.

Interestingly, the average created mesopore sizes and the BET surface areas in hierarchical beta zeolites were correlated with the molecular weights of different TAA cations, i.e. higher molecular weight TAA cations result in smaller average mesopores and correspondingly larger surface areas. For example, the average mesopore size ($d_a$) of hierarchical beta is 5.5 nm for B250_TMA, while the $d_a$ values are 4.2 nm and 3.1 nm for B250_TPA and B250_DTA, respectively.

For high Si beta zeolites like B250, the inner surface is hydrophobic and is constructed basically from Si tetrahedrons with Al species rarely distributed throughout the framework. Thus, it would attract the hydrophobic segment of the surfactant cations in aqueous solution via hydrophobic interaction. Because the surfactant cations possess similarly structured positively charged quaternary ammonium segment, the cations with higher molecular weights usually have larger and/or longer hydrophobic alkyl chains that would preferentially interact with hydrophobic zeolite surfaces. This leads to better protection of zeolite framework with less exposed surfaces for base leaching that ultimately results in smaller average mesopores.

Hierarchical beta zeolites via base leaching in CTA and DTA show distinct pore size distribution (PSD) as compared to those obtained with other TAA cationic surfactants with much narrower distribution around 3.5 nm and 3.1 nm for CTA and DTA, respectively. It is believed that this type of PSD comes from molecular self-assembly of cationic surfactants hexadecyltrimethylammonium bromide (CTAB) and dodecyltrimethylammonium bromide (DTAB) at the current experimental conditions. According to the force balance theory, the potential molecular self-assembly building units need to be composed of at least one attractive segment and one repulsive segment with properly-set force balance in between rendered at different experimental conditions.

The long hexadecyl and dodecyl hydrocarbon chains are typical attractive segments for molecular self-assembly since they can easily attract nearby hydrocarbon chains via hydrophobic interaction. The cationic quaternary ammonium head groups are the repulsive segment that will repel each other via electrostatic repulsive force. Molecular self-assembly dynamically proceeds when the attractive and repulsive forces reach a state of force balance. For similar structured cations like OTA, DTA and CTA, the hydrophobic attractive force increases with increasing hydrocarbon chain length.

Also, since the repulsive segments are identical for the surfactant molecules, the repulsive force should remain nearly the same. At the same experimental condition, the force balance between the attractive and repulsive segments should occur earlier and the self-assembly is more favorable with smaller critical micellar concentration (cmc) as the hydrocarbon chain length increases. This explains why the self-assembly of other surfactants like octyltrimethylammonium bromide (OTAB) does not proceed since it needs higher cmc in aqueous alkaline solution than the one applied in this work. Under the current experimental conditions, only the self-assembly of CTAB and DTAB occurred.

Table 3 shows the average mesopore sizes for B250 beta zeolites treated with different PDA cationic surfactants along with the molecular weight of PDA cations characterized by $N_2$ physisorption. The $N_2$ sorption isotherms and pore size distribution for hierarchical B250 beta zeolites are shown in FIG. 3. All of the PDA cations are tetraalkylammonium (TAA) structured cations. Overall, the average mesopore sizes and the mesopore volumes in hierarchical beta zeolites correlate the molecular weights of different TAA cations, i.e. higher molecular weight TAA cations result in smaller average mesopores and correspondingly larger pore volumes. For example, the average mesopore size of hierarchical beta is 5.5 nm for B250_TMA, while the $d_a$ values are 4.2 nm and 3.1 nm for and B250_TPA B250 DTA, respectively.

B250 CTA shows larger average mesopores (3.5 nm) than that of B250_DTA (3.1 nm) due to the occurrence of molecular self-assembly of cationic surfactants hexadecyltrimethylammonium bromide (CTAB) and dodecyltrimethylammonuim bromide (DTAB) at the current experimental conditions. $CTA^+$ has longer alkyl chains and thus forms larger micelles that led to the formation of larger mesopores compared to $DTA^+$. Octyltrimethylammonium bromide (OTAB), a similarly structured surfactant that is smaller than both DTAB and CTAB, does not seem to undergo molecular self-assembly under these experimental conditions and so B250_OTA does not follow the expected trend of having smaller mesopores if it were to have undergone molecular self-assembly. This can be explained according to the force balance theory and the critical micellar concentration (cmc) necessary for these types of surfactants, which exhibit both attractive and repulsive segments, to undergo self-assembly. According to the theory, the force balance between the attractive and repulsive segments should occur earlier with smaller cmc, meaning that self-assembly is more favorable as the hydrocarbon chain length increases. For OTAB, a higher cmc would be required in order for self-assembly to occur. Therefore, it is the quaternary surfactants (TMA, PTA, TEA, TPA) and the linear surfactant OTA that seem to behave according to the proposed theory by which this disclosure functions (longer or bigger chains leaves less exposed surface for base leaching to occur, leading to smaller mesopores formed).

tants along with total number of carbon atoms in the non-ionic surfactants. The carbon number directly represents the number of bridging methylene groups ($-CH_2-$) or methyl groups ($-CH_3$) within the amine molecular structures of these non-ionic surfactants, which would have preferential interaction with hydrophobic zeolite inner surfaces.

Therefore, for similar (linear) structured PDA amine surfactants (EDA, DEA, DAH), an increase in total carbon number is equivalent to an increase in preferential interaction groups (bridging methylene groups or methyl groups) that would lead to better protection of the zeolite framework with less exposed surface for base leaching that ultimately results in smaller average mesopores, as in the cases of (B250_EDA, B250_DEA, B250_DAH).

For branched structured amines like TAEA, the preferential interaction with the zeolite surface is not as good as linear structured amine surfactants with identical total carbon number. For example, both DAH and TAEA have six carbon atoms in their molecular structure, but TAEA provides less ideal preferential interaction and less effective protection for zeolite inner surface due to its branched structure, thus exposing more surface area for base leaching and resulting in larger average mesopores.

TAEA still provides better protection and thus smaller average mesopore sizes, as compared to EDA, due to the triple amount of bridging methylene groups in its structure.

TAEA is less effective in terms of protecting zeolite framework (with larger average mesopores) as compared to DEA because its structure involves a four carbon linear configuration (similar to DEA), but also has a branched segment that negatively affects it interaction with zeolite surface as (compared to DEA).

TABLE 3

Average Mesopore Sizes of Hierarchical Beta B250 Zeolites and the Molecular Weight of PDA Cations

|  | B250 | B250_TMA | B250_PTA | B250_TEA | B250_TPA | B250_OTA | B250_DTA | B250_CTA |
|---|---|---|---|---|---|---|---|---|
| $d_p{}^a$/nm | — | 5.5 | 4.6 | 4.5 | 4.2 | 4.1 | 3.1 | 3.5 |
| $MW^b$ | — | 74 | 102 | 130 | 186 | 172 | 228 | 284 |

$^a$Average mesopore sizes by BJH method
$^b$Molecular weight of PDA surfactant cations in grams/mole This disclosure reports a method of manipulating hierarchical structures of high Si zeolite beta with adjustable average mesopore sizes by NaOH base leaching with different non-ionic surfactants according to their molecular structures.

Figure 2:
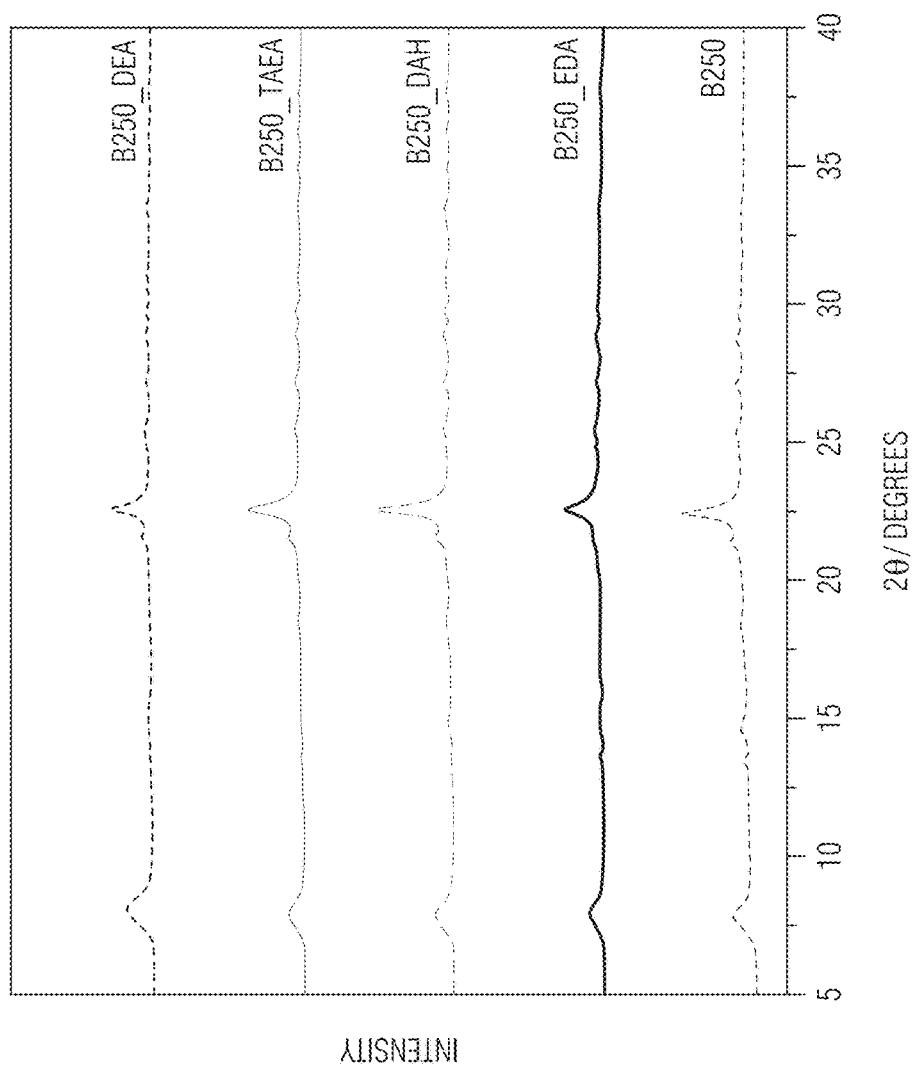
FIG. 2 depicts XRD patterns of B250 series beta zeolites with non-ionic surfactants, according to some embodiments of the disclosure.

As shown in FIG. 2, all of the selected non-ionic surfactants served as effective PDAs in protecting the parent beta framework and directing mesopore formation with well-preserved crystalline structures as compared to microporous beta B250. The applied non-ionic surfactants are various amine molecules with linear or branched structures.

Table 4 shows the average mesopore sizes for B250 beta zeolites treated with different PDA non-ionic amine surfac-

TABLE 4

Average Mesopore Sizes and Mesopore Volumes of Hierarchical Beta B250 Zeolites and the Number of Carbon Atoms in the PDA Molecular Structure of Non-Ionic Amine Surfactants

|  | B250 | B250_EDA | B250_DEA | B250_DAH | B250_TAEA |
|---|---|---|---|---|---|
| $d_p{}^a$/nm | — | 7.5 | 6.2 | 5.4 | 6.9 |
| $C^b$ | — | 2 | 4 | 6 | 6 |

$^a$Average mesopore sizes by BJH method
$^b$Number of carbon atoms in the PDA structure of non-ionic amine surfactants This disclosure reports a method of fabricating hierarchical structures of high Si zeolite beta with larger average mesopores by NaOH base leaching with non-ionic surfactant as PDAs, as compared to NaOH base leaching with cationic surfactant PDAs at the same experimental conditions.

The data demonstrates that hierarchical beta zeolites via base leaching with non-ionic surfactants possess larger mesopores than those treated with TAA cationic surfactants. Considering tetraethylammonium hydroxide (TEAOH) is the structure-directing agent for beta synthesis, it is reasonable to surmise that the TAA-type cationic surfactants would be better accommodated within the inner channel of beta framework and interact more favorably with zeolite inner surface as compared to non-ionic surfactants, which results in smaller created mesopores.

This effect could also be substantiated by comparing $d_a$ values for hierarchical zeolite derived from different cationic and non-ionic surfactants with identical carbon numbers, e.g., $C_4$ surfactants DEA ($d_a$: 6.2 nm) and TMA ($d_a$: 5.5 nm), or $C_6$ surfactants DAH ($d_a$: 5.4 nm)/TAEA ($d_a$: 6.9 nm) and PTA ($d_a$: 4.6 nm). In both cases, the presence of non-ionic surfactants resulted in the creation of larger mesopores. From the above analysis, it is concluded that it is feasible to manipulate mesopore sizes ($d_a$: 2-8 nm) in high Si beta zeolites B250 by applying different surfactants as PDAs, while the structures and surface charges of these surfactants determine the efficiency of base leaching and mesopore formation.

This effect could also be substantiated by comparing $d_a$ values for hierarchical zeolite derived from different cationic and non-ionic surfactants with identical carbon numbers, e.g., $C_4$ surfactants DEA ($d_a$: 6.2 nm) and TMA ($d_a$: 5.5 nm), or $C_6$ surfactants DAH ($d_a$: 5.4 nm)/TAEA ($d_a$: 6.9 nm) and PTA ($d_a$: 4.6 nm). In both cases, the presence of non-ionic surfactants resulted in the creation of larger mesopores. From the above analysis, it is concluded that it is feasible to manipulate mesopore sizes ($d_a$: 2-8 nm) in high Si beta zeolites B250 by applying different surfactants as PDAs, while the structures and surface charges of these surfactants determine the efficiency of base leaching and mesopore formation.

Although the findings were obtained from B250 beta zeolite, the results are not only applicable to B250, but can be generalized, within a certain range of Si/Al, to other high Si beta zeolites, such as B50 (Si/Al: 50) and B14 (Si/Al:14). To verify this, hierarchical beta zeolites were synthesized using microporous beta B50 via base leaching with the addition of several representative cationic and non-surfactants. It was found that all the conclusions we draw for B250-series hierarchical zeolites are also valid for B50-series. Table 5 shows the representative results for B50 and B14 series beta zeolites.

TABLE 5

Average mesopore sizes of hierarchical beta B50 and B14 zeolites

| | B50_TMA | B50_TPA | B50_EDA | B50_DEA | B14_TMA | B14_TPA | B14_EDA | B14_DEA |
|---|---|---|---|---|---|---|---|---|
| $d_p^a$/nm | 4.5 | 3.7 | 6.6 | 5.5 | 2.3 | 2.2 | 3.5 | 3.6 |

$^a$Average mesopore sizes by BJH method

Figure 4:
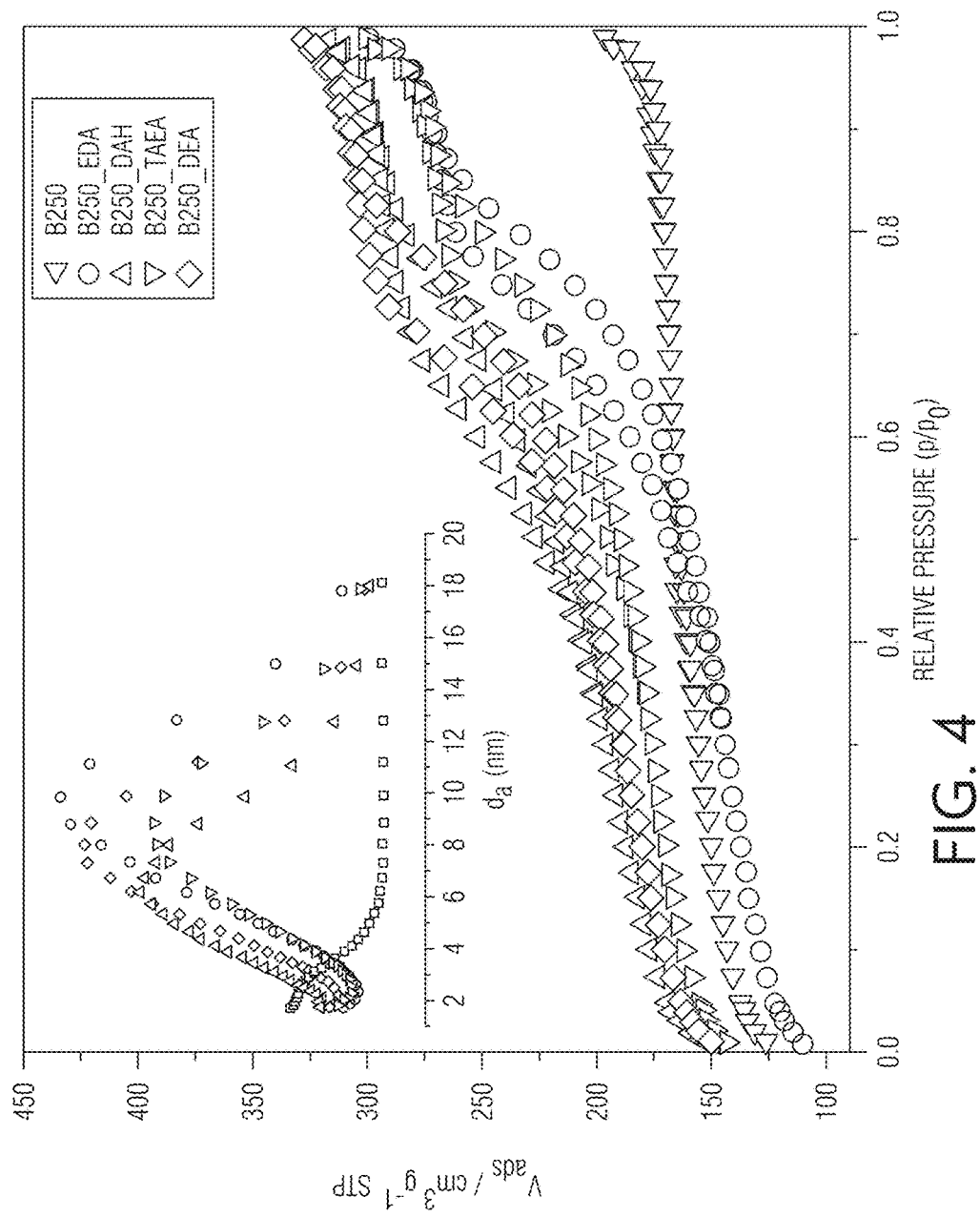
FIG. 4 depicts $N_2$ sorption isotherms of B250 series beta zeolites with non-ionic surfactants, according to some embodiments of the disclosure, wherein the insets illustrate the mesopore size distribution estimated by the BJH method.
Figure 5:
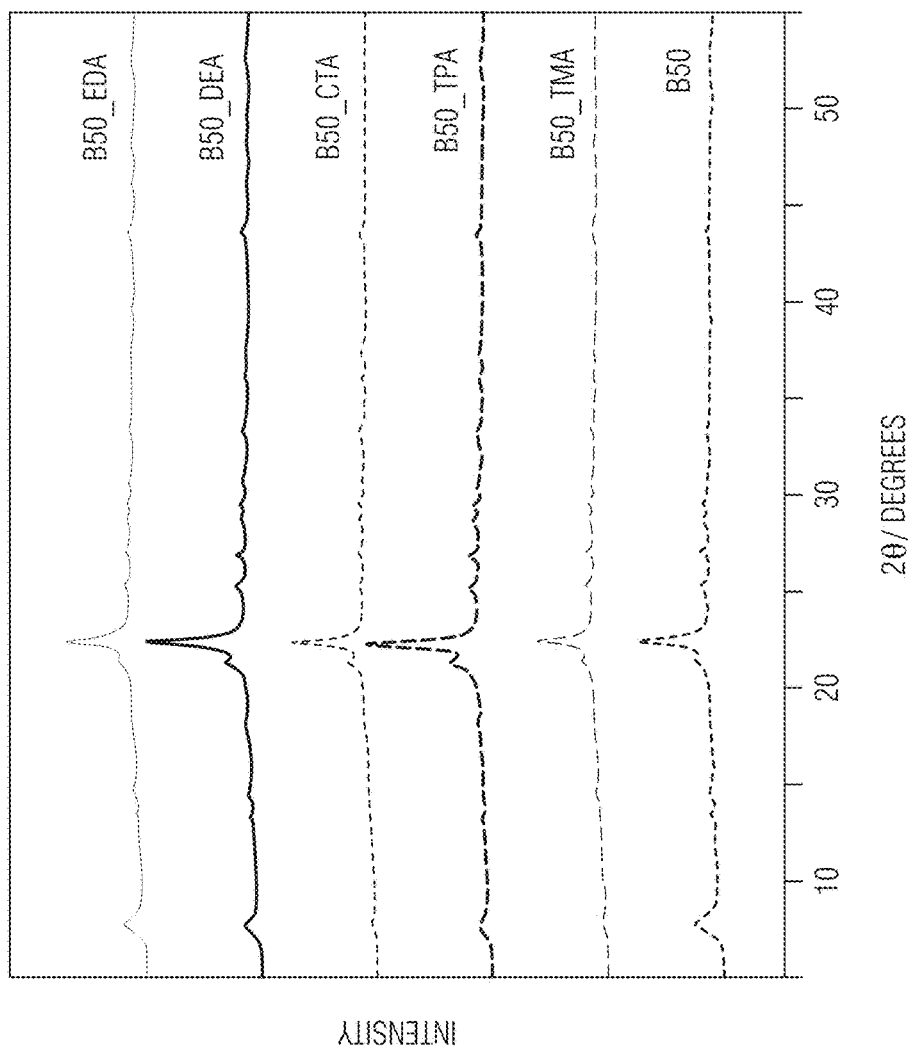
FIG. 5 depicts XRD patterns of B50 series samples, according to some embodiments of the disclosure.
Figure 6:
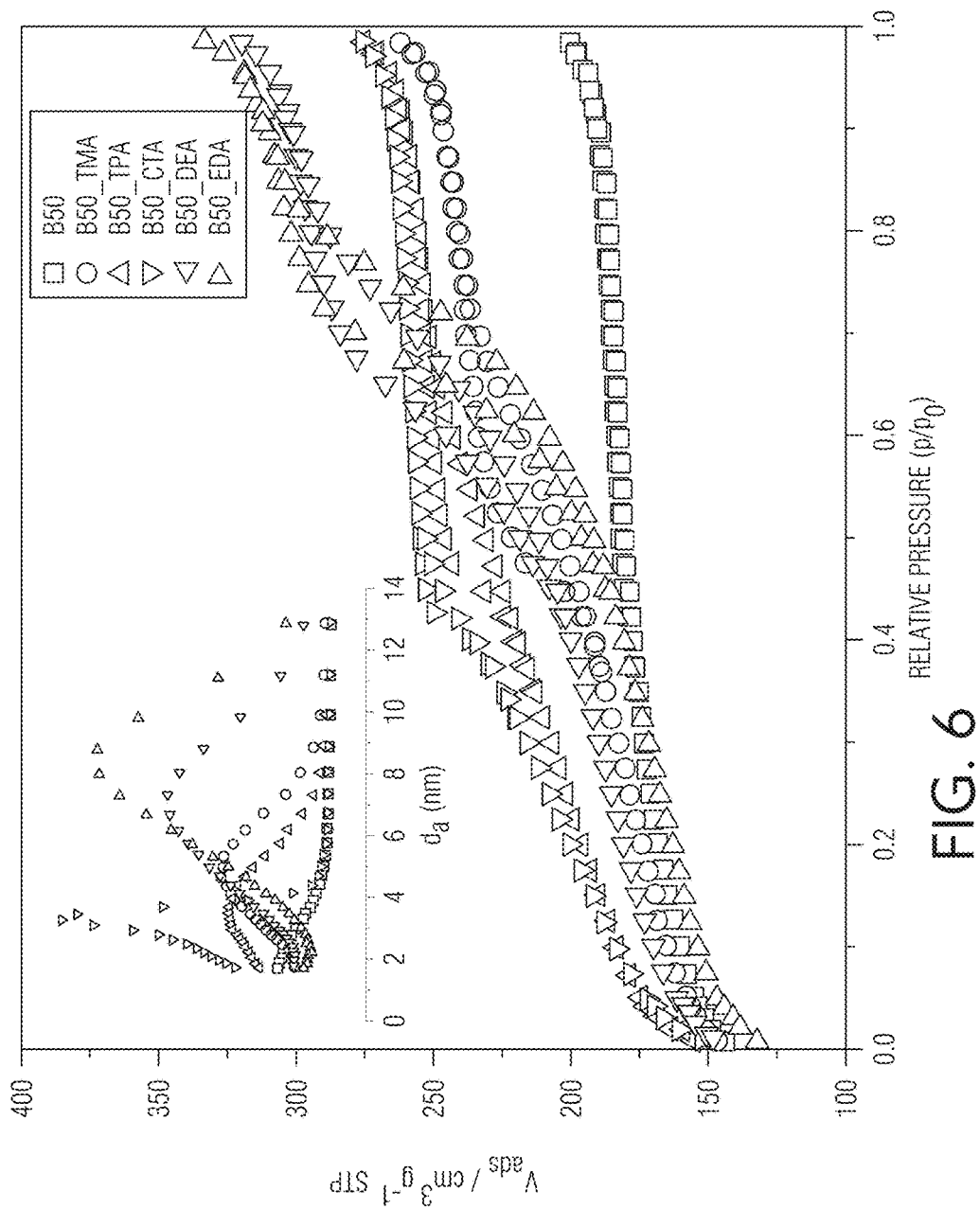
FIG. 6 depicts $N_2$ sorption isotherms of B50 series samples, according to some embodiments of the disclosure, where the insets illustrate the mesopore size distribution estimated by BJH method.

The XRD patterns (See, FIG. 5) show sharp characteristic peaks of hierarchical beta zeolites, while the initial $N_2$ uptakes are comparable to that of B50 for all samples (See, FIG. 3 and FIG. 4).

Mesopores with different sizes were created as evidenced by unique desorption hysteresis loops initiating at different $P/P_o$. Therefore, both cationic and non-ionic surfactants could be used as effective PDAs in directing the mesopore formation in alkaline solutions for high Si beta B50 without sacrificing microporosity and crystallinity of parent beta zeolites.

Again, larger mesopores are created when non-ionic surfactants are used as PDAs. Notably, the structure-property ($d_a$) relationship for B250-series also works for B50-series derived from alkaline treatments in the presence of different PDA surfactants. The distinct PSD of B50_CTA is due to the self-assembly of CTAB used in the alkaline treatment. The high pore volumes in PSD of B50_EDA and B50_DEA are believed to be exclusively due to the larger mesopores created in these hierarchical zeolites, rather than the self-assembly of non-ionic surfactants EDA and DEA.

While non-ionic surfactants could theoretically self-assemble in aqueous solutions with hydration force as the repulsive force, it seems unlikely in this work considering the fact that the current experimental conditions are not favorable for the self-assembly of OTAB, a surfactant with much stronger attractive force rendered by long alkyl chains as discussed in the previous section.

TABLE 6

POROUS PROPERTIES OF ZEOLITE BETA TREATED WITH DIFFERENT PDAs
t-plot method for $V_{mic}$, $V_{total}$, $S_{ext}$, and $S_{mic}$; $V_{mes} = V_{total} - V_{mic}$; $S_{ext}$ and $S_{mic}$
are external and micropore surface areas, respectively.

| No. | Sample | $S_{BET}/m^2g^{-1}$ | $V_{mes}{}^b/cm^3g^{-1}$ | $V_{mic}{}^b/cm^3g^{-1}$ | $S_{ext}{}^b/m^2g^{-1}$ | $S_{mic}{}^b/m^2g^{-1}$ | $d_a{}^c/nm$ |
|---|---|---|---|---|---|---|---|
| 1 | B250 | 569 | 0.01 | 0,18 | 144 | 425 | — |
| 2 | B250_TMA | 600 | 0.11 | 0.17 | 159 | 441 | 5.5 |
| 3 | B250_PTA | 647 | 0.18 | 0.18 | 179 | 468 | 4.6 |
| 4 | B250_TEA | 684 | 0.19 | 0.19 | 190 | 494 | 4.6 |
| 5 | B250_TPA | 718 | 0.21 | 0.19 | 234 | 484 | 4.2 |
| 6 | B250_OTA | 693 | 0.20 | 0.19 | 226 | 467 | 4.1 |
| 7 | B250_DTA | 753 | 0.29 | 0.14 | 327 | 426 | 3.1 |
| 8 | B250_CTA | 779 | 0.43 | 0.11 | 249 | 530 | 3.5 |
| 9 | B250_EDA | 510 | 0.30 | 0.13 | 175 | 335 | 7.5 |
| 10 | B250_DAH | 708 | 0.28 | 0.19 | 225 | 484 | 5.4 |
| 11 | B250_TAEA | 649 | 0.24 | 0.19 | 165 | 485 | 6.9 |
| 12 | B250_DEA | 682 | 0.30 | 0.19 | 208 | 473 | 6.2 |
| 13 | B50 | 647 | 0.01 | 0.20 | 146 | 501 | — |
| 14 | B50_TMA | 664 | 0.20 | 0.18 | 199 | 465 | 4.5 |
| 15 | B50_TPA | 731 | 0.23 | 0.18 | 279 | 452 | 3.7 |
| 16 | B50_CTA | 727 | 0.27 | 0.15 | 376 | 352 | 3.1 |
| 17 | B50_EDA | 612 | 0.33 | 0.16 | 213 | 400 | 6.6 |
| 18 | B50_DEA | 676 | 0.30 | 0.18 | 232 | 444 | 5.5 |
| 19 | B14 | 681 | 0.01 | 0.22 | 101 | 580 | — |
| 20 | B14_TMA | 701 | 0.16 | 0.18 | 243 | 458 | 2.3 |
| 21 | B14_TPA | 736 | 0.18 | 0.19 | 263 | 473 | 2.2 |
| 22 | B14_CTA | 726 | 0.16 | 0.19 | 255 | 471 | 2.1 |
| 23 | B14_EDA | 687 | 0.21 | 0.17 | 274 | 413 | 3.6 |
| 24 | B14_DEA | 701 | 0.22 | 0.17 | 294 | 407 | 3.6 |

It should be noted that the increasing amount of Al species in zeolite framework not only alters the preferential interaction between zeolite surface and PDA surfactants, but more importantly, it enhances the framework resistance toward alkaline leaching since the negatively charged framework by the existence of Al hinders the hydrolysis of Si—O—Al bonds in the presence of hydroxide ions.

For B14 beta zeolites, its hierarchical structure can be created directly by a NaOH leaching with good preservation of microporosity ($d_a$: ~4 nm) at the same experimental conditions. In the presence of different surfactant PDAs, the alkaline leaching directed the formation of smaller mesopores in B14 series zeolites due to the protection of surfactants with less exposed surfaces for mesopore creation.

Figure 7:
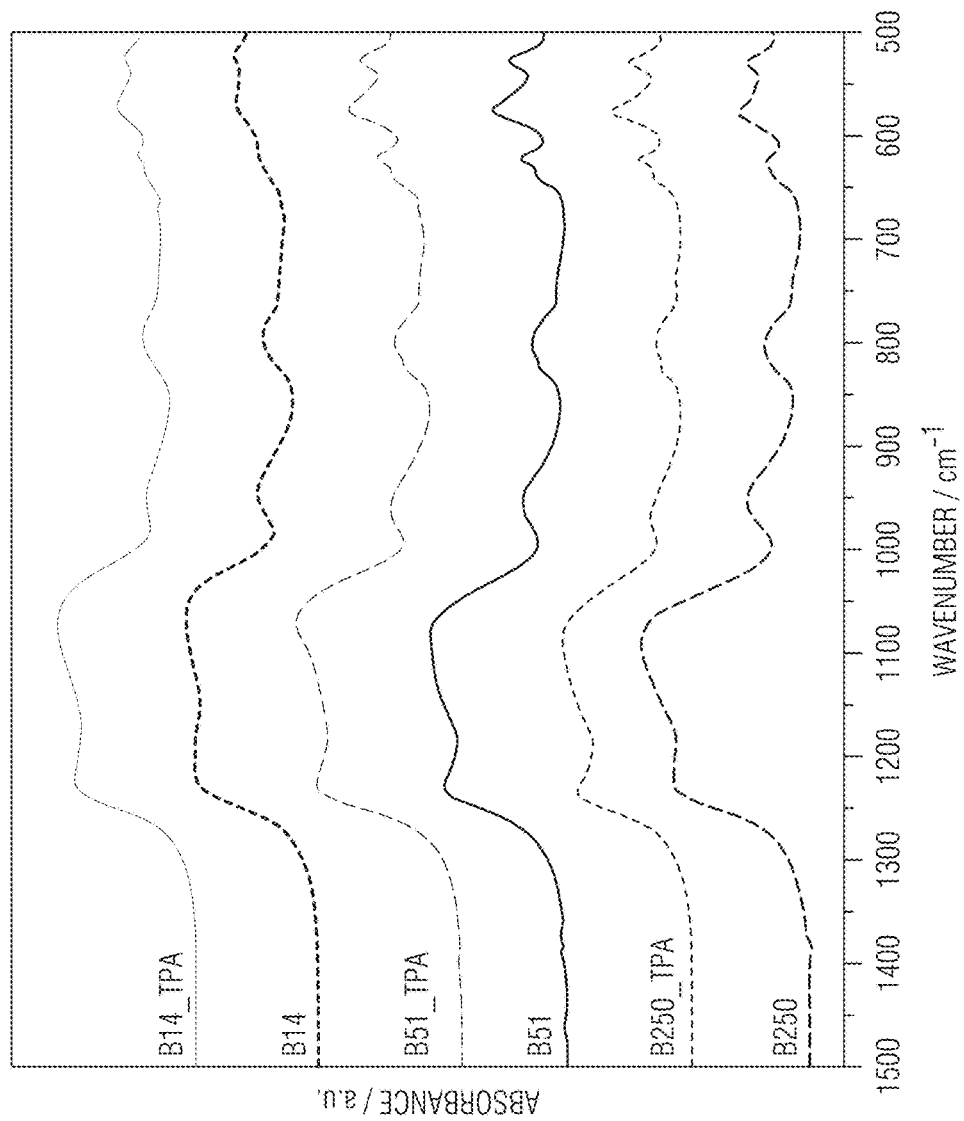
FIG. 7 depicts Fourier Transform Infrared (FT-IR) spectra of different beta zeolites in skeletal vibration region according to some embodiments of the disclosure.
Figure 8:
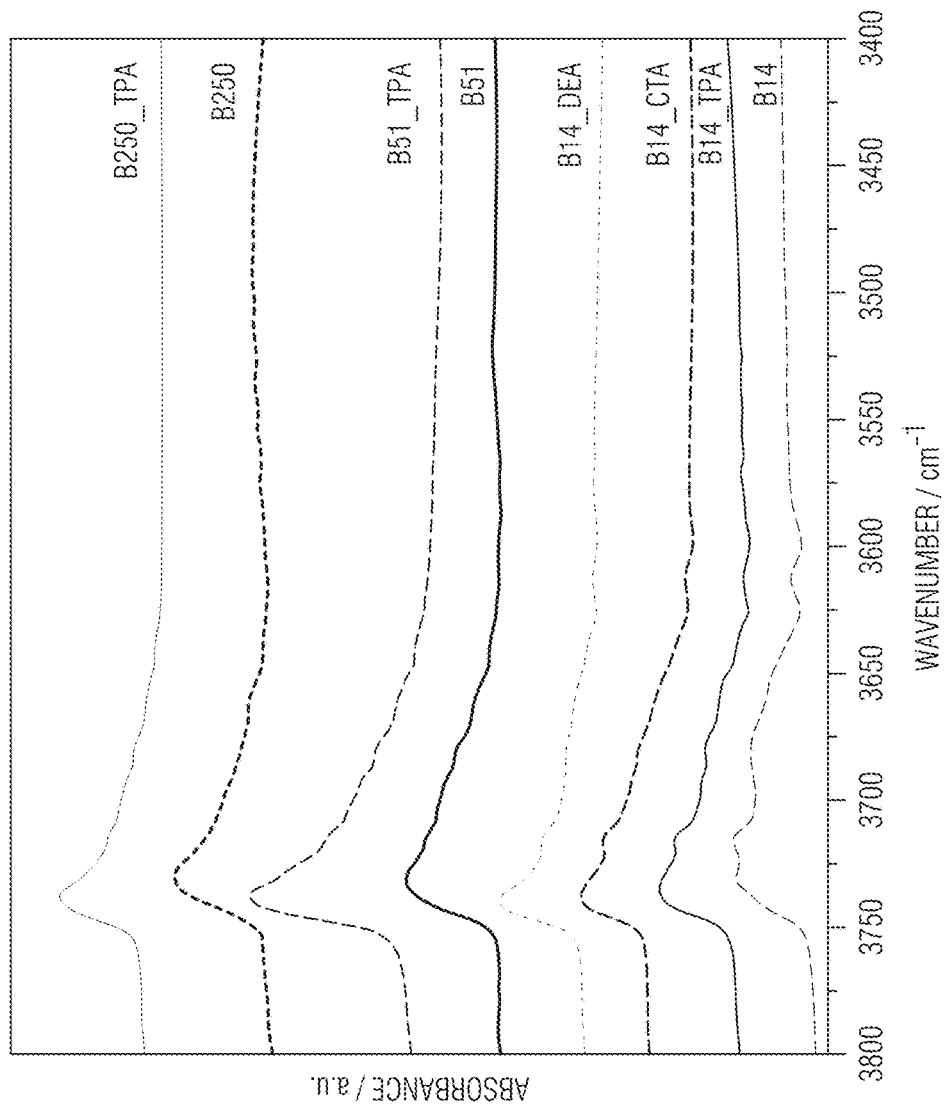
FIG. 8 depicts FT-IR spectra of different beta zeolites in OH-stretching region, according to some embodiments of the disclosure.

FIG. 7 shows the FT-IR spectra of different beta zeolites in skeletal vibration and FIG. 8 shows the FT-IR spectra of different beta zeolites in OH-stretching region. It can be seen that the intensities of the 575 and 525 $cm^{-1}$ bands, which are characteristic of zeolite beta, are maintained upon alkaline leaching in NaOH solutions with PDAs as compared to their respective parent zeolites, indicating that the framework of zeolite beta was well-preserved during the formation of hierarchical structure, which is consistent with the XRD characterization.

The bands at around 1075 $cm^{-1}$ and 800 $cm^{-1}$ represent the O-T-O asymmetric and symmetric stretching vibration, respectively. They shift linearly with the content of the framework Al, i.e., the wavenumber increases with decreasing Al content in zeolites. The absorptions at 1240 $cm^{-1}$ and 950 $cm^{-1}$ are probably due to the internal tetrahedral within parent and hierarchical zeolites, which are also indicative of good preservation of crystallinity.

During the process of mesopore creation via alkaline leaching, well-preserved microporosity and crystalline structure usually translate to well-preserved acidity, which is critical for the obtained hierarchical zeolites to be used as heterogeneous catalysts. The acidic property of beta zeolites with different Si/Al ratios was examined by OH-stretching vibration IR spectra for representative samples.

The absorption band at 3740 $cm^{-1}$ is attributed to the terminal silanol groups. It is clear that the intensity of this band increases for leached samples, which should be due to the creation of mesopores with more exposed external surfaces and terminal silanol groups. On the contrary, the changes in the adsorption at 3720 $cm^{-1}$ (internal hydroxyl groups at defect sites) before and after alkaline treatments are not significant.

The samples of B14 series exhibit the strongest intensity at this absorption band among all beta series (B14, B50, and B250). This is attributed to the higher amounts of Al species that are transformed into octahedral positions during high-temperature treatments for H-B14 samples. According to $^{27}Al$ MAS NMR characterization, both framework and non-framework Al species exist in H-beta zeolites after calcination, while the as-treated beta (Na-form) zeolites only possess framework tetrahedral Al. The octahedral Al sites result in the creation of internal hydroxyl groups as revealed by the absorption at 3720 $cm^{-1}$.

At 3610 $cm^{-1}$, the absorption comes from the existence of bridging hydroxyl groups that is related directly to Brønsted acidity. As shown for B14 series, after alkaline base leaching with different surfactants, the bands are distinct but with slightly reduced intensities. For high Si zeolites B50 and B250 samples, the absorption bands at 3610 $cm^{-1}$ are not discernable due to the limited amounts of Al in the framework. The catalytic activity of different beta zeolites was evaluated by the liquid phase α-pinene isomerization.

Figure 9:
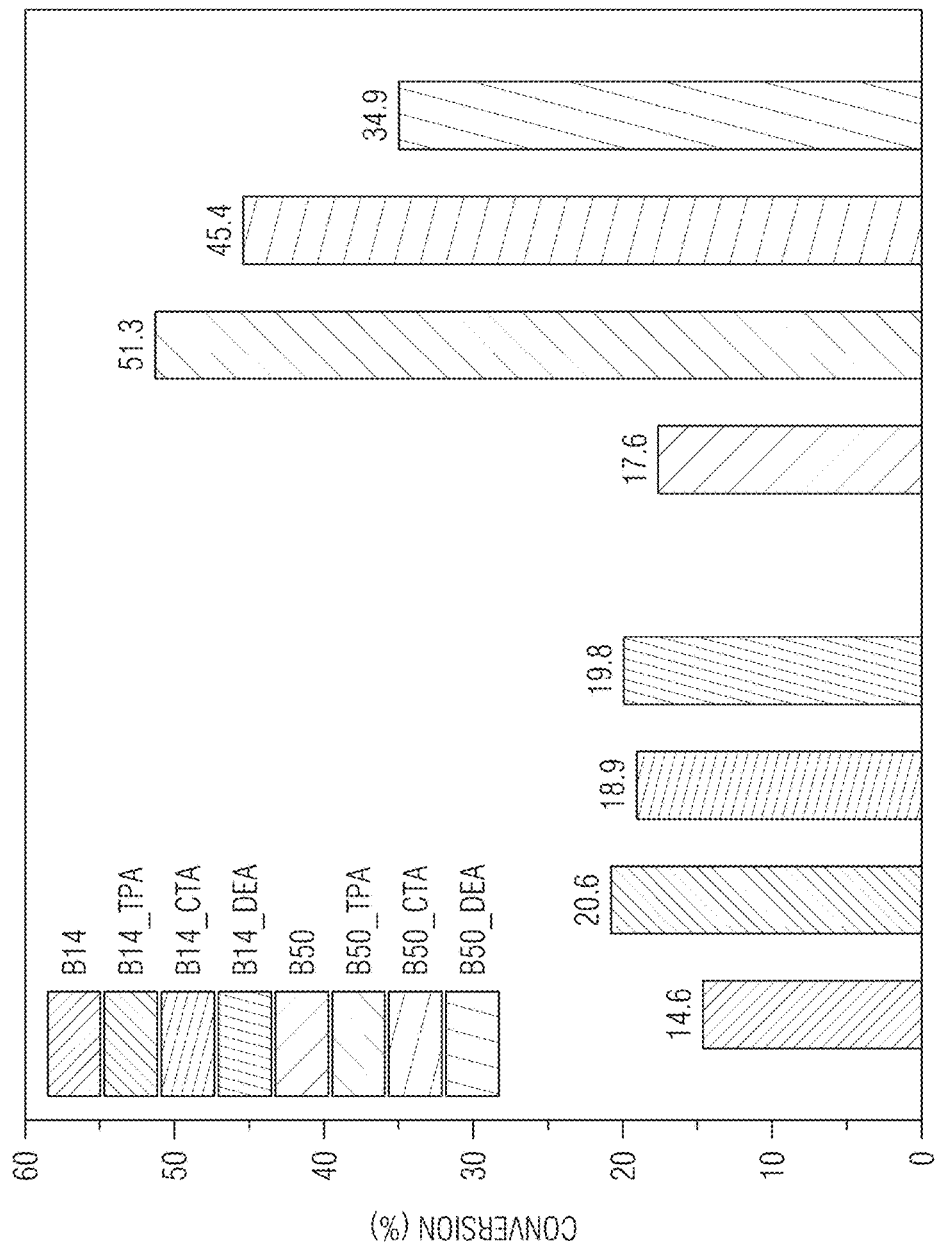
FIG. 9 depicts the α-pinene conversion of different parent and hierarchical beta zeolites (70° C., 30 min, 0.1 g of catalyst, 2.0 mL of α-pinene), according to some embodiments of the disclosure.

FIG. 9 illustrates the total conversion of α-pinene over representative beta catalysts. B250 parent and the corresponding leached hierarchical zeolites provided negligible conversion and therefore were not included in the figure. The lack of catalytic activity for B250 series of beta zeolites is mainly attributed to the very limited amounts of Al within zeolite framework, since α-pinene isomerization is a Brønsted acid catalyzed reaction.

Meanwhile, the α-pinene conversions for B14 and B50 parent zeolites are 14.6% and 17.6%, respectively. The conversion increases significantly with increasing Al contents in parent zeolites, as compared to B250. On the other hand, similar conversions for B14 and B50 parent beta zeolites suggested that the effective acidic sites are comparable, which is probably due to the inaccessibility of Al sites originated from diffusion limitation.

For base leached hierarchical beta zeolites, both B14 and B50 series show improved conversions. The conversion of treated B14 series increased by more than 30% as compared to parent B14, while B50 series experienced much more significant improvements, i.e. B50_TPA exhibited three times as high as B50 parent beta. These results indicate that the acidity of beta is preserved during base leaching and the enhanced catalytic activity results from the more favored mass transfer in hierarchical zeolites for reactants and products, due to the presence of mesoporosity.

Moreover, it seems that there is an optimal range of Al contents (or Si/Al ratio) to achieve the highest catalytic activity, and the conversion of α-pinene does not monotonically increase with increasing Al contents in beta zeolites. This is consistent with the report that the H-beta zeolites containing both micro- and mesopores with $SiO_2/Al_2O_3$ ratio of 55-66 exhibited the highest catalytic activity in α-pinene isomerization.

FIG. 9 also shows that hierarchical beta treated in the presence of CTA (B14_CTA and B50_CTA) exhibited high α-pinene conversion and no activity degradation was observed. It was reported for USY that the CTA self-assembly might lead to the formation of amorphous mesoporous molecular sieves (MMS) and the final products were composites of hierarchical zeolites and MMS, resulting in no enhancement of catalytic activity.

Figure 10:
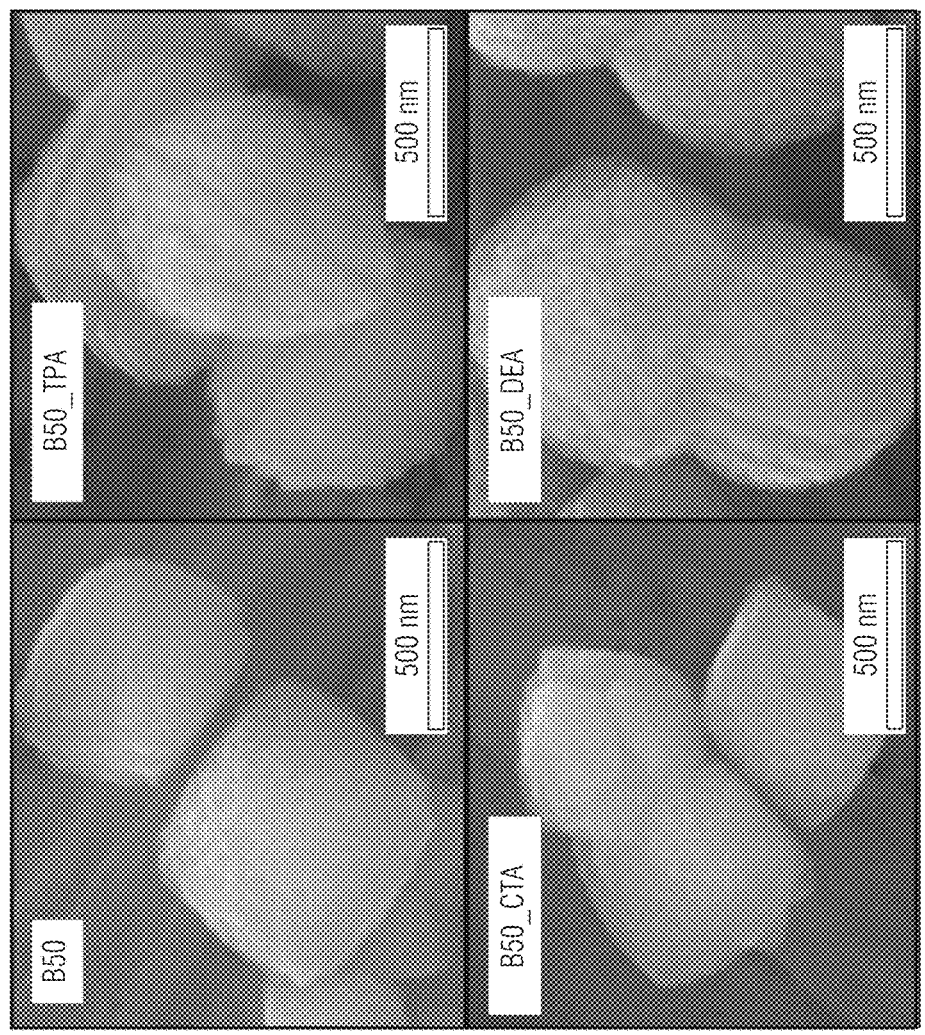
FIG. 10 depicts Scanning Electron Microscopy (SEM) images of parent and base-leached beta zeolites (B50 series), according to some embodiments of the disclosure.

This was not the case for beta zeolites in this work as revealed by the enhanced conversions as well as well-preserved crystal morphologies (See FIG. 10). Note that the formation of mesopores by base leaching is achieved by partial dissolution and recrystallization of parent zeolites, which might affect to some extent the amounts of acid sites as discussed previously in FT-IR characterization.

However, with an appropriate selection of starting beta zeolites as well as PDAs, the benefits of adding a tailored mesoporosity are dominant and would ultimately result in significantly improved conversions for reactions containing bulky molecules that are otherwise difficult to access the acid sites due to diffusion limitation.

This work demonstrated the tailoring of hierarchical structures in beta zeolites of differing Al contents is achieved through top-down alkaline treatments with 11 different cationic and non-ionic surfactants as PDAs. Notably, all of the applied surfactants are effective PDAs in directing the mesopore formation in alkaline solutions without experiencing significant decrease in microporosity and crystallinity of parent beta zeolites.

Moreover, the structure-property relationship was established between surfactant structure and average mesopore sizes in resulting hierarchical zeolites, especially for high Si beta zeolites when the presence of PDA is necessary to avoid framework amorphization during NaOH desilication. The average created mesopores can be manipulated in the range of 2-8 nm by applying different cationic or non-ionic surfactants with various molecular weights or molecular structures. And, the optimized hierarchical beta zeolites exhibited much higher catalytic conversions in liquid phase isomerization of α-pinene than parent beta zeolites.

This work demonstrated the feasibility of tailoring the mesopore structures by a top-down base leaching with rational selection of PDAs for zeolite beta and it is believed that this strategy has the potential to be generalized and optimized for more types of zeolites.

Having described the subject matter of the present disclosure in detail and by reference to specific embodiments, it is noted that the various details described in this disclosure should not be taken to imply that these details relate to elements that are essential components of the various embodiments described in this disclosure, even in cases where a particular element is illustrated in each of the drawings that accompany the present description. Rather, the claims appended hereto should be taken as the sole representation of the breadth of the present disclosure and the corresponding scope of the various embodiments described in this disclosure. Further, it will be apparent that modifications and variations are possible without departing from the scope of the appended claims.

The invention claimed is:

1. A method for producing mesoporous beta zeolites comprising:
providing parent beta zeolites having a molar ratio of silicon to aluminum of at least 10;
selecting a target average mesopore size between 2 nm and 8 nm for the parent beta zeolites;
selecting a pore directing agent (PDA) based on the target average mesopore size, where a small cationic surfactant is selected as the PDA when the target average mesopore size is at least 5 nm, and a large cationic surfactant is selected as the PDA when the target average mesopore size is less than 5 nm, where the large cationic surfactant has a molecular weight of greater than 100 grams/mole, and the small cationic surfactant has a molecular weight of less than 100 grams/mole;
adding the selected PDA to an alkaline solution to form a PDA-base mixture; and
adding the parent beta zeolites to the PDA-base mixture to produce the mesoporous beta zeolites having an average mesopore size corresponding to the target average mesopore size.

2. The method of claim 1, wherein the molar ratio of silicon to aluminum is from 14 to 300.

3. The method of claim 1, wherein the molar ratio of silicon to aluminum is from 50 to 250.

4. The method of claim 1, wherein the large cationic surfactant and the small cationic surfactant are quaternary ammonium compounds.

5. The method of claim 1, wherein the selected PDA is the large cationic surfactant, the large cationic surfactant comprising dodecyltrimethylammonium, cetyltrimethylammonium, prop yltrimethylammonium, tetraethylammonium, tetrapropylammonium, octyltrimethylammonium, or combinations thereof.

6. The method of claim 1, wherein the selected PDA is the small cationic surfactant and comprises tetramethylammonium.

7. The method of claim 1, wherein the alkaline solution comprises NaOH, KOH, or CsOH.

8. The method of claim 7, wherein the alkaline solution comprises NaOH.

9. The method of claim 1, wherein the mesoporous beta zeolites have a BET surface area greater than 700 $m^2/g$ and the average mesopore size is less than 5 nm.

10. The method of claim 1, wherein the mesoporous beta zeolites have a BET surface area less than 700 m$^2$/g and the average mesopore size is at least 5 nm.

11. A method for producing mesoporous beta zeolites comprising:
providing parent beta zeolites having a molar ratio of silicon to aluminum of at least 10;
selecting a pore directing agent (PDA) based on the target average mesopore size, where a large cationic surfactant is selected as the PDA when the target average mesopore size is less than 5 nm;
adding the PDA comprising cationic surfactant having a molecular weight of more than 100 grams/mole to an alkaline solution to form a PDA-base mixture; and
adding the parent beta zeolites to the PDA-base mixture to produce the mesoporous beta zeolites having an average size of less than 5 nm.

12. The method of claim 11, wherein the molar ratio of silicon to aluminum is from 14 to 300.

13. The method of claim 11, wherein the molar ratio of silicon to aluminum is from 50 to 250.

14. The method of claim 11, wherein the mesoporous beta zeolites have a BET surface area greater than 700 m$^2$/g.

15. A method for producing mesoporous beta zeolites comprising:
providing parent beta zeolites having a molar ratio of silicon to aluminum of at least 10;
selecting a pore directing agent (PDA) based on the target average mesopore size, where a small cationic surfactant is selected as the PDA when the target average mesopore size is at least 5 nm;
adding the PDA comprising cationic surfactant having a molecular weight of less than 100 grams/mole to an alkaline solution to form a PDA-base mixture; and
adding the parent beta zeolites to the PDA-base mixture to produce the mesoporous beta zeolites having an average size of at least 5 nm.

16. The method of claim 15, wherein the molar ratio of silicon to aluminum is from 14 to 300.

17. The method of claim 15, wherein the molar ratio of silicon to aluminum is from 50 to 250.

18. The method of claim 15, wherein the mesoporous beta zeolites have a BET surface area less than 700 m$^2$/g.

19. A method of for producing mesoporous beta zeolites comprising:
providing parent beta zeolites having a molar ratio of silicon to aluminum of at least 10;
selecting a pore directing agent (PDA) based on the target average mesopore size, where a non-ionic surfactant is selected as the PDA when the target average mesopore size is at least 2 nm;
adding the PDA comprising a non-ionic surfactant to an alkaline solution to form a PDA-base mixture; and
adding the parent beta zeolites to the PDA-base mixture to produce the mesoporous beta zeolites having an average mesopore size greater than 2 nm.

20. The method of claim 19, wherein the molar ratio of silicon to aluminum is from 14 to 300.

21. The method of claim 19, wherein the molar ratio of silicon to aluminum is from 50 to 250.

22. The method of claim 19, wherein the amine compound has from 2 to 6 carbon atoms.

23. The method of claim 19, wherein the mesoporous beta zeolites have a BET surface area less than 700 m$^2$/g.

24. The method of claim 19, wherein the non-ionic surfactant is a linear amine compound having more than 2 carbon atoms.

25. The method of claim 24, wherein the linear amine compound has from 2 to 6 carbon atoms.

26. The method of claim 24, wherein the number of carbon atoms present in the linear amine compound is inversely proportional to the target average mesopore size.

27. The method of claim 19, wherein the non-ionic surfactant comprises monoamines, polyamines, or combinations thereof.

28. The method of claim 19, wherein the non-ionic surfactant comprises ethylenediamine (EDA), diaminohexane (DAH), trisaminoethylamine (TAEA), diethylamine (DEA), or combinations thereof.

29. The method of claim 19, wherein the non-ionic surfactant is a branched amine compound having more than 2 carbon atoms.

30. The method of claim 29, wherein the branched amine compound has from 2 to 6 carbon atoms.

31. The method of claim 29, wherein the average mesopore size is greater than 5 nm.

* * * * *

UNITED STATES PATENT AND TRADEMARK OFFICE
CERTIFICATE OF CORRECTION

PATENT NO. : 10,391,480 B2  
APPLICATION NO. : 15/583380  
DATED : August 27, 2019  
INVENTOR(S) : Ke Zhang et al.

Page 1 of 1

It is certified that error appears in the above-identified patent and that said Letters Patent is hereby corrected as shown below:

On the Title Page

Item (56), other publications, cite no. 6, delete "Verboekend et al., "Hierarchical Y and USY Zeolites Designed by Post-Synthetic Strategies", Adv. Fund. Mater., 2012, 22, 916-928, Wiley-VCH Verlag GmbH & Co. cited by applicant" and insert --Verboekend et al., "Hierarchical Y and USY Zeolites Designed by Post-Synthetic Strategies", Adv. Funct. Mater., 2012, 22, 916-928, Wiley-VCH Verlag GmbH & Co. cited by applicant--, therefor.

In the Specification

In Column 6, Line 8, delete "(TPA)" and insert --(TPA$^+$)--, therefor.  
In Column 12, Line 4, delete "B250 TMA" and insert --B250_TMA--, therefor.  
In Column 13, Line 10, delete "and B250_TPA B250 DTA" and insert --B250_TPA and B250_DTA--, therefor.  
In Column 13, Line 12, delete "B250 CTA" and insert --B250_CTA--, therefor.

In the Claims

In Column 20, Claim 5, Line 55, delete "prop yltrimethylammonium" and insert --propyltrimethylammonium--, therefor.

Signed and Sealed this  
Twenty-ninth Day of October, 2019

Andrei Iancu  
*Director of the United States Patent and Trademark Office*